United States Patent [19]

Shiokawa et al.

[11] Patent Number: 4,590,272
[45] Date of Patent: May 20, 1986

[54] PESTICIDAL 1-(SUBSTITUTED BENZYL)-2-NITROMETHYLENE-TETRAHYDROPYRIMIDINES

[75] Inventors: Kozo Shiokawa, Kanagawa; Shinzo Kagabu; Shinichi Tsuboi, both of Tokyo, Japan

[73] Assignee: Nihon Tokushu Noyaku Seizo K.K., Tokyo, Japan

[21] Appl. No.: 657,323

[22] Filed: Oct. 3, 1984

[30] Foreign Application Priority Data

Oct. 6, 1983 [JP] Japan ................................. 58-185854

[51] Int. Cl.⁴ ........................................... C07D 239/02
[52] U.S. Cl. ..................................... 544/335; 548/342
[58] Field of Search .......................... 544/335; 514/256

[56] References Cited

U.S. PATENT DOCUMENTS 3,948,934  4/1976  Tieman et al. ........................ 548/353

FOREIGN PATENT DOCUMENTS 2514402  10/1976  Fed. Rep. of Germany .
2732660   2/1979  Fed. Rep. of Germany .

OTHER PUBLICATIONS

Sinharay et al., Chem. Abst. 86-43734 k DE 2514402.

Primary Examiner—Donald G. Daus
Assistant Examiner—C. Shen
Attorney, Agent, or Firm—Sprung, Horn, Kramer & Woods

[57] ABSTRACT

Pesticidally active novel nitromethylene-tetrahydropyrimidines of the formula

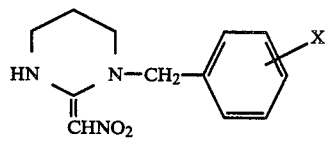

(I)

wherein X represents a halogen atom.

9 Claims, No Drawings

PESTICIDAL 1-(SUBSTITUTED BENZYL)-2-NITROMETHYLENE-TETRAHYDROPYRIMIDINES

DETAILED DESCRIPTION OF THE INVENTION

This invention relates to novel nitromethylene-tetrahydropyrimidine derivatives, a process for the production thereof, and an insecticidal, miticidal and nematocidal agent having such derivatives as active ingredients.

More specifically, this invention relates to novel nitromethylene-tetrahydropyrimidine derivatives represented by the following general formula (I).

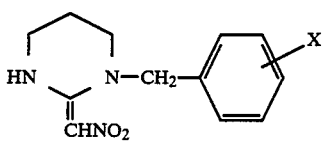
(I)

wherein X represents a halogen atom.

The nitromethylene-tetrahydropyrimidine derivatives of formula (I) in accordance with this invention can be produced by the following general process (i) to which the invention also pertains.

Process (i)

A process for producing the nitromethylene-tetrahydropyrimidine derivatives of general formula (I), which comprises reacting a compound of the general formula

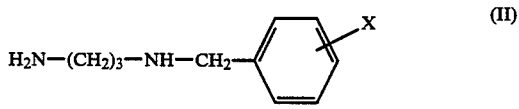
(II)

wherein X is as defined above, with 1-nitro-2,2-bis(methylthio)ethylene of the formula

The present invention further relates to an insecticidal, miticidal and nematocidal agent comprising the nitromethylene-tetrahydropyrimidine derivative of general formula (I) as an active ingredient.

German Offenlegungsschrift No. 2,514,402 known before the filing date of the present application states that 2-nitromethylene-imidazolidine derivatives and 2-nitromethylene-hexahydropyrimidine derivatives of the following general formula

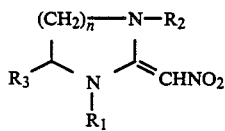

exhibit insecticidal activity. The above general formula includes cases of $n=2$, $R_1$=phenyl-($C_1$-$C_2$)alkyl group and $R_2$=$R_3$=hydrogen and the specification of the German Offenlegungsschrift No. 2,514,402 describes a compound of the following formula:

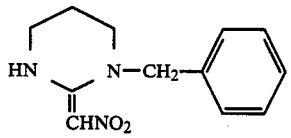
(A-1)

However, $R_1$ in the above general formula does not embrace a benzyl group having a substituent.

It has now been found, that the new nitromethylene-tetrahydropyrimidine compounds of general formula (I) process outstanding controlling activity against noxious insects, mites or ticks, and nematodes.

The nitromethylene-tetrahydropyrimidine derivatives of the invention represented by the above general formula (I) are not encompassed by the general formula described in the above-cited German Offenlegungsschrift, nor described in any prior technical literature.

The compounds of this invention are characterized by the fact that in their chemical structure, 2-nitromethylene-tetrahydropyrimidine is a basic skeleton and a halogen-substituted benzyl group is substituted at the nitrogen atom at the 1-position of the tetrahydropyrimidine ring. The phenyl nucleus is substituted by halogen preferably in the 3- or 4-position.

It has also been found that the compounds of this invention have quite outstanding controlling activity over the compound of formula (A-1) which is described in the above-cited German Offenlegungsschrift No. 2,514,402 and is most similar to the compounds of this invention, and that the compounds of this invention exhibit a marked controlling effect against noxious insects which have developed resistance to organic phosphate and carbamate type insecticides through long-term use, particularly sucking insects such as aphids, planthoppers and leafhoppers.

It has further been found that the compounds of the invention exhibit particularly superior controlling effects when applied to a water surface, and in regard to residual effects in water, are far superior to compounds very analogous to the compounds of this invention, for example the compound of formula (A-1) given hereinabove.

It is an object of this invention to provide the novel nitromethylene-tetrahydropyrimidine derivatives of general formula (I), a process for production thereof, and the use thereof as an insecticidal, miticidal and nematocidal agent.

The above and other objects and advantages of this invention will become more apparent from the following description.

The active compounds of this invention exhibit an accurate controlling effect against noxious insects, mites or ticks, and nematodes without causing any phytotoxicity to cultivated plants. Furthermore, the compounds of this invention can be used for control and eradication of a wide range of pests, including sucking insects, biting insects and other plant parasites, pests on stored grains and pests causing health hazards.

Examples of the pests are shown below.

Coleopterous insects

*Callosobruchus chinensis,*
*Sitophilus zeamais,*
*Tribolium castaneum,*
*Epilachna vigitioctomaculata,*
*Agriotes fuscicollis,*

*Anomala rufocuprea,*
*Leptinotarsa decemkineata,*
*Diabrotica* spp.,
*Monochamus alternatus,*
*Lissorhoptrus oryzophilus,* and
*Lyctus brunneus.*

Lepidopterous insects

*Lymantria dispar,*
*Malacosoma neustria,*
*Pieris rapae,*
*Spodoptera litura,*
*Mamestra brassicae,*
*Chilo suppressalis,*
*Pyrausta nubilalis,*
*Ephestia cautella,*
*Adoxophyes orana,*
*Carpocapsa pomonella,*
*Agrotis fucosa,*
*Galleria mellonella,*
*Plutella maculipennis,* and
*Phyllocnistis citrella.*

Hemipterous insects

*Nephotettix cincticeps,*
*Nilaparvata lugens,*
*Pseudococcus cometocki,*
*Unaspis yanonensis,*
*Myzus persicas,*
*Aphis pomi,*
*Aphis gossypii,*
*Rhopalosiphum pseudobrassicas,*
*Stephanitis nashi,*
Nazara spp.,
*Cimex lectularius,*
*Trialeurodes vaporariorum,* and
Psylla spp.

Orthopterous insects

*Blatella germanica,*
*Periplaneta americana,*
*Gryllotalpa africana,* and
*Locusta migratoria migratoriodes.*

Isopterous insects

*Deucotermes speratus,* and
*Coptotermes formosanus.*

Dipterous insects

*Musca domestica,*
*Aedes aegypti,*
*Hylemia platura,*
*Culex pipens,*
*Anopheles sinensis,* and
*Culex tritaeniorhynchus.*

Mites

*Tetranychus telarius,*
*Panonychus citri,*
*Aculus pelekassi,* and
Tnrronomus spp.

Nematodes

*Meloidogyne incognita,*
*Bursaphelenchus lignicolus* Mamiya et Kiyohara,
*Aphelenchoides besseyi,*
*Beterodera glycines,* and
*Pratylenchus* spp.

In the field of veterinary medicine, the novel compounds of this invention are effective against various noxious animal parasites (endo- and ecto-parasites) such as ticks, insects and worms. Examples of such animal parasites are shown below.

Ticks

Oranithodoros spp,
Ixodes spp., and
Boophilus spp.

Insects

Gastrophilus spp.,
Stomoxys spp.,
Trichodectes spp.,
Rhodnius spp., and
*Ctenocephalides canis.*

Substances having pesticidal activity against all of these pests may sometimes be referred to in this application simply as insecticides.

The nitromethylene-tetrahydropyrimidine derivatives of general formula (I) of this invention can be easily produced, for example, by the following process (i).

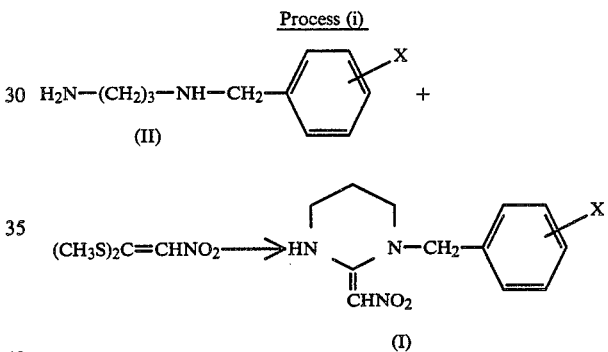

(In the formulae, X is as defined above.)

In the above reaction scheme, X represents a halogen atom, specifically a fluoro, chloro, bromo or iodo atom.

In the process for producing the compound of general formula (I) shown by the above reaction scheme, specific examples of the starting compound of general formula (II) include N-(3-chlorobenzyl)trimethylenediamine, N-(4-chlorobenzyl)trimethylenediamine, N-(4-bromobenzyl)trimethylenediamine and N-(4-fluorobenzyl)trimethylenediamine.

By citing the following typical example, the above process is described specifically.

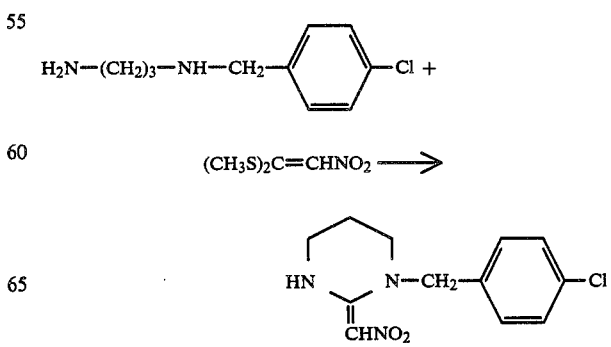

Desirably, the above process for producing the compound of this invention can be carried out using a solvent or a diluent. For this purpose, all inert solvents and diluents can be used.

Examples of such solvents or diluents include water; aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride trichloroethylene and chlorobenzene; ethers such as diethyl ether, methyl ethyl ether, diisopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; alcohols such as methanol, ethanol, isopropanol, butanol and ethylene glycol; esters such as ethyl acetate and amyl acetate; acid amides such as dimethylformamide and dimethylacetamide; sulfones and sulfoxides such as dimethyl sulfoxide and sulfolane; and bases such as pyridine.

The above process can be carried out over a wide temperature range. Generally, it can be carried out at a temperature between about −20° C. and the boiling point of the mixture, desirably between about 0° C. and about 100° C. Desirably, the reaction is carried out under normal atmospheric pressure, but it is also possible to operate under elevated or reduced pressures.

The compound of general formula (I) in accordance with this invention may also be produced by a different process (ii) schematically shown below.

Process (ii)

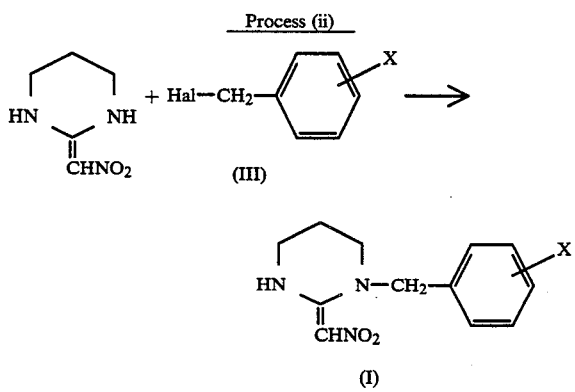

(In the formula, X is as defined above, and Hal represents a halogen atom.)

In the process for producing the compound of general formula (I) shown by the above reaction scheme, specific examples of the compound of general formula (III) include 3-chlorobenzyl chloride, 4-chlorobenzyl chloride, 4-bromobenzyl chloride and 4-fluorobenzyl chloride. The corresponding bromides can also be cited.

By citing the following referential example, the process (ii) is described below specifically.

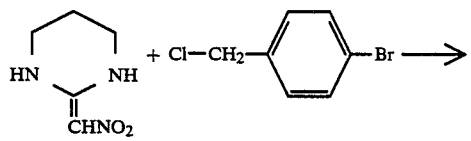

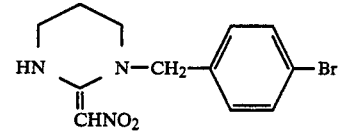

The above process can be carried out by using the same inert solvents and diluents as exemplified with regard to the process (i).

The above reaction may be carried out in the presence of an acid binder. Examples of the acid binder may include the hydroxides, carbonates, bicarbonates and alcoholates of alkali metals and tertiary amines such as triethylamine, diethylaniline and pyridine, all of which are generally used.

The process (ii), as in the case of process (i) can be practiced over a wide temperature range, and desirably under normal atmospheric pressure. It is also possible to operate under elevated or reduced pressures.

As an insecticidal, miticidal and nematocidal agent, the compound of this invention may be used directly upon dilution with water, or in various formulations obtained by methods generally practiced in the production of agricultural chemicals using agriculturally acceptable adjuvants. In actual use, these various formulations may be applied directly or after diluting them with water to the desired concentrations.

The agriculturally acceptable adjuvants as referred to herein include, for example, diluents (solvents, extenders, carriers), surface-active agents (solubilizing agents, emulsifiers, dispersing agents, wetting agents), stabilizers, stickers, aerosol propellants and synergists.

Examples of the solvents are water, and organic solvents, for example hydrocarbons [such as n-hexane, petroleum ether, petroleum fractions (e.g., paraffin waxes, kerosene, light oils, middle oils, and heavy oils), benzene, toluene, and xylene], halogenated hydrocarbons (such as methylene chloride, carbon tetrachloride, ethylene chloride, ethylene dibromide, chlorobenzene and chloroform), alcohols (such as methanol, ethanol, propanol and ethylene glycol), ethers (such as diethyl ether, ethylene oxide and dioxane), alcohol ethers (such as ethylene glycol monomethyl ether), ketones (such as acetone and isophorone), esters (such as ethyl acetate and amyl acetate), amides (such as dimethylformamide and dimethylacetamide) and sulfoxides (such as dimethyl sulfoxide).

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (such as pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfonic acid esters (such as sodium laurylsulfate), arylsulfonic acids (such as alkylarylsulfonic acid salts and sodium alkylnaphthalenesulfonates), succinic acid salts, and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chlorides) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (such as agricultural soaps, casein lime, sodium alginate, polyvinyl alcohol, vinyl acetate-type adhesives and acrylic adhesives); aerosol propellants (such as trichlorofluoromethane, dichlorofluoromethane, 1,2,2-trichloro-1,1,2-trifluoroethane, chlorobenzene, LNG, and lower ethers); combustion controlling agents for fumigants (such as nitrites, zinc powder, and dicyandiamide); oxygen-yielding agents (such as chlorates); effect-prolonging agents; dispersion stabilizers [such as casein, tragacanth, carboxymethyl cellulose (CMC), and polyvinyl alcohol (PVA)]; and synergists.

The compounds of this invention can be formulated into various forms by methods generally practiced in the production of agricultural chemicals. Illustrative of such forms are emulsifiable concentrates, oil preparations, wettable powders, soluble powders, suspensions, dusts, granules, pulverulent preparations, fumigants, tablets, aerosols, pastes and capsules.

The insecticidal, miticidal and nematocidal agent of this invention may contain about 0.1 to about 95% by weight, preferably about 0.5 to about 90% by weight, of the aforesaid active ingredient.

In actual use, the suitable amount of the active compound in the aforesaid various formulations and ready-to-use preparations is generally about 0.0001 to about 20% by weight, preferably about 0.005 to about 10% by weight.

The content of the active ingredient can be properly varied depending upon the type of the formulation, the method, purpose, time and locus of its application, the state of occurrence of noxious insects, mites or ticks, and nematodes.

If required, the compounds of this invention may be used in combination with other agricultural chemicals, for example other insecticides, fungicides, other miticides, other nematocides, antiviral agents, herbicides, plant growth regulators and attractants (such as organophosphate compounds, carbamate compounds, dithio (or thiol) carbamate compounds, organochlorine compounds, dinitro compounds, organosulfur or organometallic compounds, antibiotics, substituted diphenyl ether compounds, urea compounds, and triazine compounds), and/or fertilizers.

Various formulations and ready-to-use preparations containing the aforesaid active ingredient of the invention can be applied by various methods generally practiced in the field of agricultural chemical application, for example spraying (liquid spraying, misting, atomizing, dusting, granule scattering, water surface application, pouring, etc.); fumigation; soil application (mixing, sprinkling, vaporing, pouring, etc.); surface application (coating, banding, powder coating, covering, etc.); dipping; and baiting. It can also be used by the so-called ultralow volume spraying method. According to this method, the active ingredient may be included in an amount of 100%.

The rate of application per unit area is, for example, about 0.03 to about 10 kg, preferably about 0.3 to about 6 kg, per hectare. In special cases, however, it may, and sometimes should, be outside the specified range.

According to this invention, there can be provided an insecticidal, miticidal and nematocidal composition comprising the compound of general formula (I) as an active ingredient and a diluent (a solvent and/or an extender and/or a carrier) and/or a surface-active agent, and if further required, a stabilizer, a sticker, a synergist, etc.

This invention also provides a method for controlling noxious insects, mites or ticks, and nematodes, which comprises applying to a noxious insect, mite or tick, or nematode and/or its habitat or the locus of its occurrence the compound of general formula (I) alone or in admixture with a diluent (a solvent and/or an extender and/or a carrier) and/or a surface-active agent and if further required, a stabilizer, a sticker, a synergist, etc.

The following examples illustrate the present invention specifically. It should be noted however that the invention is not limited to these specific examples alone.

EXAMPLE 1

N-(4-chlorobenzyl)trimethylenediamine (8.45 g) and 1-nitro-2,2-bis(methylthio)ethylene (6.60 g) were heated under reflux in 100 ml of ethanol for 16 hours. The reaction mixture was cooled to room temperature, and the precipitated crystals were collected by filtration and washed with a small amount of ethanol to give 1-(4-chlorobenzyl)-2-(nitromethylene)tetrahydropyrimidine (9.8 g) represented by the following formula. Melting point: 172°–174° C.

(compound No. 1)

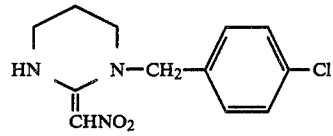

Table 1 below shows the compounds of this invention which were synthesized in the same way as in Example 1 by using corresponding starting materials

TABLE 1

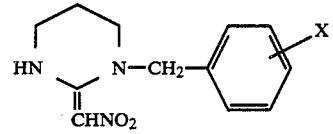

| Compound No. | X | Physical constant (m.p., °C.) |
|---|---|---|
| 2 | 3-Cl | 190–192 |
| 3 | 4-Br | 198–199 |
| 4 | 4-F | 171–173 |

EXAMPLE 2

(wettable powder)

Fifteen parts of compound No. 1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and sprayed onto a noxious insect, mite or nematode and/or its habitat or the locus of its occurrence.

EXAMPLE 3

(emulsifiable concentrate)

Thirty parts of compound No. 3 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and sprayed onto a noxious insect, mite or nematode and/or its habitat or the locus of its occurrence.

EXAMPLE 4

(dust)

Two parts of compound No. 4 of the invention and 98 parts of powdery clay are pulverized and mixed to form a dust. It is scattered over a noxious insect, mite or nematode and/or its habitat or the locus of its occurrence.

EXAMPLE 5

(granules)

Water (25 parts) is added to a mixture consisting of 10 parts of compound No. 2 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over a noxious insect, mite or nematode and/or its habitat or the locus of its occurrence.

EXAMPLE 6

(granules)

Ninety-five parts of clay mineral particles having a particle size distribution between 0.2 and 2 mm are put in a rotary mixer, and with rotation, 5 parts of compound No. 3 of the invention is sprayed onto the particles to wet them uniformly. The wet mixture is dried at 40° to 50° C. to form granules. The granules are scattered over a noxious insect, mite or nematode and/or its habitat or the locus of its occurrence.

EXAMPLE 7

(oil preparation)

Compound No. 1 of this invention (0.5 part) and 99.5 parts of kerosene are mixed and stirred to form an oil preparation. It is sprayed onto a noxious insect, mite or nematode and/or its habitat or the locus of its occurrence.

EXAMPLE 8

(biological test)

Test on *Nephotettix cincticeps* having resistance to organophosphorus agents:

Preparation of a test chemical

Solvent: 3 parts by weight of xylene
Emulsifier: 1 part by weight of polyoxyethylene alkyl phenyl ether To form a suitable preparation, 1 part by weight of the active compound was mixed with the aforesaid amount of the solvent containing the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over the rice plants, and 30 female imagoes of *Nephotettix cincticeps* showing resistance to organophosphorus agents were released into the net. The pots were each placed in a constant temperature chamber and the number of dead insects was examined 24 hours later, and the kill ratio was calculated.

The results are shown in Table 2.

TABLE 2

| Compound No. | Concentration of the active ingredient (ppm) | Kill ratio (%) |
|---|---|---|
| 1 | 8 | 100 |
| 2 | 8 | 100 |
| 3 | 8 | 100 |
| 4 | 8 | 100 |
| Comparison A-1 | 40 | 60 |

Note
(1) The compound numbers are the same as given above.
(2) Comparison A-1 shows the following compound which is given hereinabove.

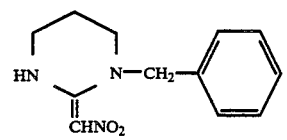

EXAMPLE 9

(biological test)

Test on *Myzus persicas* (green peach aphids) having resistance to organophosphorus agents:

Testing method

Green peach aphids which had been bred were inoculated on eggplant seedlings (black elongated eggplants), about 20 cm tall, grown in unglazed pots having a diameter of 15 cm (about 200 aphids per seedling). One day after the inoculation, a water dilution of each active compound at a predetermined concentration prepared as in Example 8 was sprayed in a sufficient amount onto the plants using a spray gun. After the spraying, the pots were left to stand in a greenhouse at 28° C. Twenty-four hours after the spraying, the kill ratio was calculated. For each compound, the test was carried out through two replicates.

The results are shown in Table 3.

TABLE 3

| Compound No. | Concentration of the active ingredient (ppm) | Kill ratio (%) |
|---|---|---|
| 1 | 200 | 100 |
| 3 | 200 | 100 |
| 4 | 200 | 100 |
| Comparison A-1 | 1000 | 80 |
| | 200 | 30 |
| Estox (commercially | 1000 | 100 |
| | 200 | 20 |

TABLE 3-continued

| Compound No. | Concentration of the active ingredient (ppm) | Kill ratio (%) |
|---|---|---|
| available) | | |

Note
1 The compound numbers and comparison A-1 are the same as above.
2 Estox: S—2-ethylsulfinyl-1-methylethyldimethyl-phosphorothiolate (45% emulsifiable concentrate).

It will be appreciated that the instant specification and examples are set forth by way of illustration and not limitation, and that various modifications and changes may be made without departing from the spirit and scope of the present invention.

What is claimed is:

1. A 1-halobenzyl-2-(nitromethylene)tetrahydropyrimidine of the formula

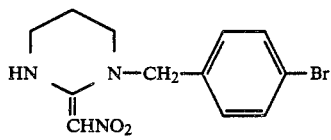

in which X is a halogen atom.

2. A compound according to claim 1, wherein X is in 4-position on the phenyl ring.

3. A compound according to claim 1, wherein such compound is 1-(4-chlorobenzyl)-2-(nitromethylene)tetrahydropyrimidine of the formula

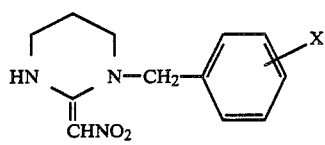

4. A compound according to claim 1, wherein such compound is 1-(3-chlorobenzyl)-2-(nitromethylene)tetrahydropyrimidine of the formula

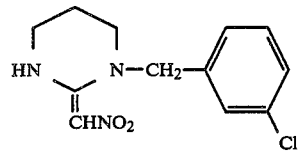

5. A compound according to claim 1, wherein such compound is 1-(4-bromobenzyl)-2-(nitromethylene)tetrahydropyrimidine of the formula

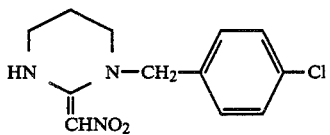

6. A compound according to claim 1, wherein such compound is 1-(4-fluorobenzyl)-2-(nitromethylene)tetrahydropyrimidine of the formula

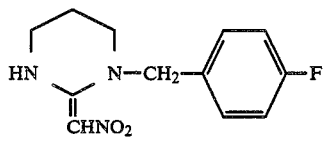

7. An insecticidal, miticidal or nematocidal composition comprising an insecticidally, miticidally or nematocidally effective amount of a compound according to claim 1 in admixture with a diluent.

8. A method of combating insects, mites or nematodes which comprises applying thereto or to a habitat thereof an insecticidally, miticidally or nematocidally effective amount of a compound according to claim 1.

9. The method according to claim 8, wherein such compound is
1-(4-chlorobenzyl)-2-(nitromethylene)tetrahydropyrimidine,
1-(3-chlorobenzyl)-2-(nitromethylene)tetrahydropyrimidine,
1-(4-bromobenzyl)-2-(nitromethylene)tetrahydropyrimidine or
1-(4-fluorobenzyl)-2-(nitromethylene)tetrahydropyrimidine.

* * * * *